United States Patent

Senanayake et al.

[11] Patent Number: 6,147,217
[45] Date of Patent: Nov. 14, 2000

[54] SYNTHESIS OF TERFENADINE AND DERIVATIVES

[75] Inventors: Chris Hugh Senanayake, Shrewsbury; Qun Kevin Fang, Wellesley; Scott Harold Wilkinson, Shrewsbury, all of Mass.

[73] Assignee: Sepracor Inc., Marlborough, Mass.

[21] Appl. No.: 09/316,104

[22] Filed: May 24, 1999

Related U.S. Application Data

[62] Division of application No. 08/803,895, Feb. 4, 1997, Pat. No. 5,925,761.

[51] Int. Cl.$^7$ .................. C07D 211/22; C07D 211/34
[52] U.S. Cl. .................. 546/240; 546/236; 546/237; 546/239
[58] Field of Search ................. 546/236, 237, 546/239, 240

[56] References Cited

U.S. PATENT DOCUMENTS

| | | | |
|---|---|---|---|
| 3,141,024 | 7/1964 | Houssin et al. | 548/540 |
| 3,806,526 | 4/1974 | Carr et al. | 546/240 |
| 3,965,257 | 6/1976 | Carr et al. | 546/240 |
| 4,254,129 | 3/1981 | Carr et al. | 546/237 |
| 5,581,011 | 12/1996 | D'Ambra | 569/8 |
| 5,589,487 | 12/1996 | D'Ambra | 514/317 |
| 5,750,703 | 5/1998 | D'Ambra | 546/240 |

FOREIGN PATENT DOCUMENTS

| | | | |
|---|---|---|---|
| 479601 | 4/1992 | European Pat. Off. | |
| 5-97808 | 10/1991 | Japan. | |
| 537071 | of 1984 | Spain. | |
| 544321 | of 1985 | Spain. | |
| WO94/03170 | of 1994 | WIPO. | |
| WO95/00480 | of 1995 | WIPO | 211/14 |
| WO95/00482 | of 1995 | WIPO | 211/22 |
| WO95/31436 | of 1995 | WIPO | 211/22 |

OTHER PUBLICATIONS

Houssin et al. "Piperidine or pyrrolidine analgesic amides . . . " CA 59:1599B, 1964.
Maillard et al. "Anti–inflammatories dériveés de l'acide . . . "*Chimie Therapeutique 8*, 487–494 (1973).
Carr et al. "Synthesis of Terfenadine" *Arzneim.–Forsch. 32*, 1157–1159 (1982).
Kawai et al. "A Facile Synthesis of an Oxidation Product of Terfenadine" *J. Or. Chem. 59*, 2620–2622 (1994).
W. Theilheimer *Synthetic Methods of Organic Chemistry 26*, 192 (1972).

*Primary Examiner*—Ceila Chang
*Attorney, Agent, or Firm*—Heslin, & Rothenberg, P.C.

[57] ABSTRACT

Processes for preparing compounds having the general formula:

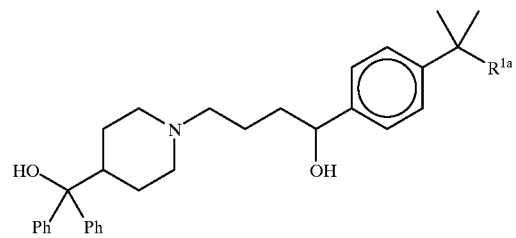

wherein R$^{1a}$ is protected carboxy, carboxy, hydroxymethyl, protected hydroxymethyl, or methyl are disclosed. Processes of the invention begin with a starting material of the general formula IV

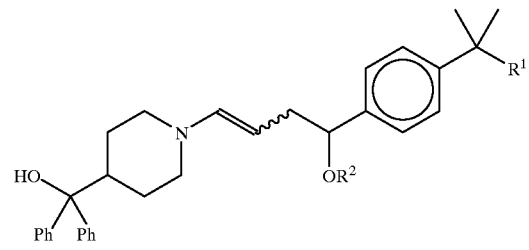

wherein R$^1$ and R$^2$ are as defined in the specification.

8 Claims, No Drawings

SYNTHESIS OF TERFENADINE AND DERIVATIVES

CROSS REFERENCE TO RELATED APPLICATION

This application is a divisional of U.S. application Ser. No. 08/803,895, filed Feb. 4, 1997, now U.S. Pat. No. 5,925,761, is incorporated herein by reference.

BACKGROUND OF THE INVENTION

1. Field of the Invention

This invention relates to processes for preparing terfenadine and derivatives thereof. In another aspect this invention relates to processes for preparing terfenadine carboxylate. In another aspect this invention relates to synthetic intermediates.

2. Description of the Related Art

Terfenadine (Formula T) is a non-sedating antihistamine sold in the U.S. under the designation "Seldane" (Hoechst Marion Roussel).

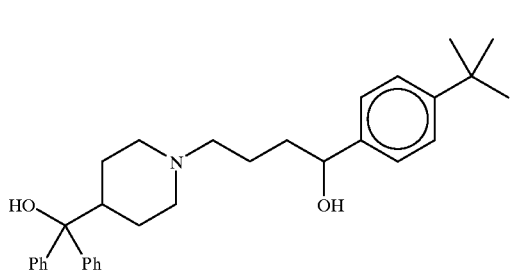

Certain derivatives of terfenadine are also known and disclosed as active antihistamines, e.g., in U.S. Pat. No. 4,254,129 (Carr et al.) The primary active metabolite of terfenadine is a compound known as terfenadine carboxylate or fexofenadine (Formula B), which is among the terfenadine derivatives disclosed in U.S. Pat. No. 4,254,129. The hydrochloride salt of terfenadine carboxylate is sold in the U.S. under the designation "Allegra" (Hoechst Marion Roussel).

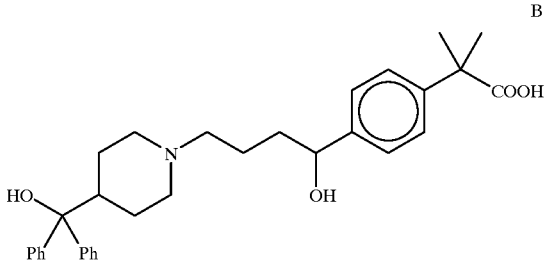

Several synthetic methods for preparing terfenadine and derivatives thereof have been disclosed. For example, Carr et al. disclose a method involving acylation of a compound of Formula C and further elaboration to provide terfenadine carboxylate.

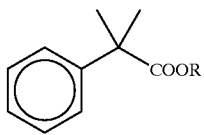

The acylation step in this method, however, is said in International Patent Application No. WO 95/00482 (D'Ambra) to provide a mixture of regioisomers that includes the 3-substituted product in addition to the desired 4-substituted product. D'Ambra provides substantially pure regioisomers, e.g., through fractional crystallization of the acylation product. Regiochemically pure 4-substituted product for use in preparing terfenadine and derivatives can also be produced using a metal-mediated coupling approach, as described in *J. Org. Chem.* 1994, 59, 2620 (Kawai et al.), where 3-butyn-1-ol is coupled to methyl 2-(4-halophenyl)-2,2-dimethylacetate.

The process of the invention described below exhibits at least two major advantages over the processes of the art: (1) It is regiospecific; the manipulative complications that arise from the presence of multiple isomers are avoided. (2) The yield from aldehyde to final product is very much higher than known processes—59% overall.

SUMMARY OF THE INVENTION

This invention provides processes for preparing compounds of Formula I

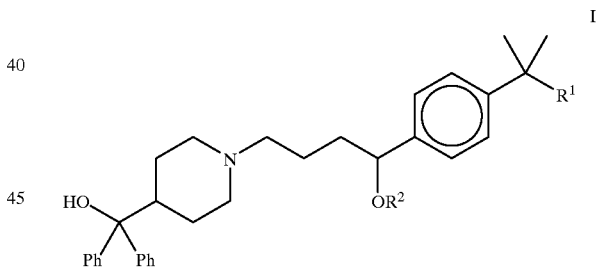

wherein $R^1$ is methyl, protected hydroxymethyl or protected carboxyl and $-OR^2$ is protected hydroxyl or hydroxyl.

In one aspect, the invention relates to a process comprising subjecting a compound of Formula IVa

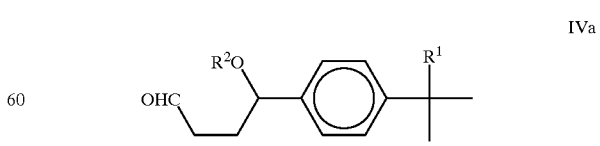

or a tautomer thereof, to reductive amination with α,α-diphenyl-4-piperidinemethanol and a reducing agent to provide a compound of Formula I

I

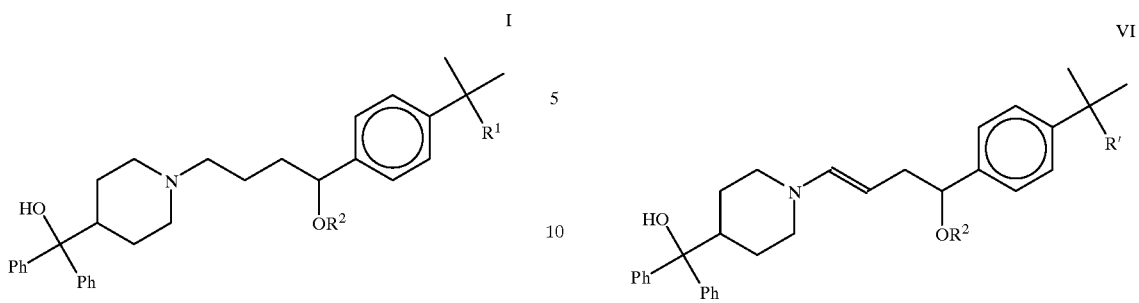

The compound of formula IVa may be prepared by treating a compound of Formula IV

IV wherein A is a precursor of a formylmethyl group, with a reagent capable of converting the precursor of a formylmethyl group to a formylmethyl group. The compound of formula IV may be prepared by contacting a compound of Formula II

II with a compound of Formula III $$(MX)[CH_2-A]_n \quad III$$

wherein MX is a cationic metal-containing moiety and n is the net valence of MX. This process provides a compound of the formula E

E in which the hydroxy group may be protected, if desired, to provide the compound of Formula IV. In a preferred embodiment, MX is MgBr and A is chosen from the group consisting of 2,2-di(lower-alkoxy)ethyl; (1,3-dioxolan-2-yl)methyl; (1,3-dioxan-2-yl)methyl; (1,3-dioxetan-2-yl)methyl; and (1,3-benzodioxolan-2-yl)methyl.

In another aspect, the invention relates to a process comprising contacting a compound of formula VI

VI with a reducing agent to provide compounds of formula

I

The compound of formula VI may be prepared by contacting a compound of Formula IVc IVc with α,α-diphenyl-4-piperidinemethanol and a reducing agent.

In either of the foregoing processes, the reducing agent may be a borohydride or aluminum hydride. When $R^1$ is protected hydroxymethyl or protected carboxyl and $R^2$ is hydrogen, an additional step of deprotecting $R^1$ to provides a compound of Formula B or D

B

-continued

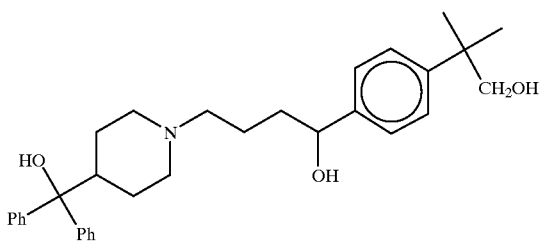

When R¹ is protected hydroxymethyl or protected carboxyl and R² is a protecting group for hydroxyl, two additional steps of deprotecting R¹ and R² provide the compounds of Formula B and D. When the protecting groups are appropriate, these two steps may be combined into a single operation.

When R¹ is methyl and R² is a protecting group for hydroxyl, an additional step of deprotecting R² provides a compound of Formula T

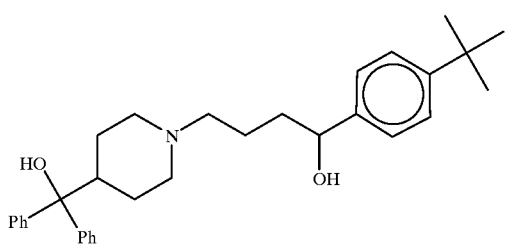

In some embodiments R¹ may be chosen from the group consisting of

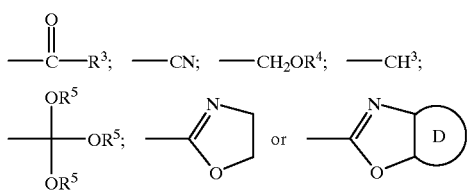

wherein D represents the residue of a 5- or 6-membered, saturated or aromatic ring. R² may be chosen from hydrogen, trialkylsilyl, benzyl, tetrahydropyran-2-yl, lower-alkylcarbonyl, arylcarbonyl and arylmethyl. The aryl group is preferably phenyl, optionally substituted with from one to three substituents each independently selected from the group consisting of lower alkyl, lower alkoxy, and halo. R³ may be chosen from: (1) alkoxy, wherein the alkoxy group contains from one to about 8 carbon atoms; (2) alkenyloxy, wherein the alkenyloxy group contains from one to about 4 carbon atoms; (3) arylmethoxy, wherein the aryl group is phenyl optionally substituted with from one to three substituents each independently selected from the group consisting of lower alkyl, lower alkoxy, and halo; and (4) —NR⁶R⁷, in which R⁶ and R⁷ are hydrogen, alkyl of 1 to 8 carbons or benzyl.

In compounds in which R¹ is —CH₂OR⁴, R⁴ may be trialkylsilyl, Li⁺, benzyl, tetrahydropyran-2-yl, lower-alkylcarbonyl, arylcarbonyl and arylmethyl, wherein the aryl group is phenyl optionally substituted with from one to three substituents each independently selected from the group consisting of lower alkyl, lower alkoxy, and halo. In compounds in which R¹ is —C(OR⁵)₃, R⁵ is alkyl of 1 to 6 carbons.

When R¹ and R⁴ are the same, deprotection of —OR¹ and —CH₂OR⁴ may be carried out in a single step.

The invention, in a particular embodiment, provides a complete process for the production of terfenadine carboxylate comprising the sequential steps of:

(a) reacting a compound of formula IIa

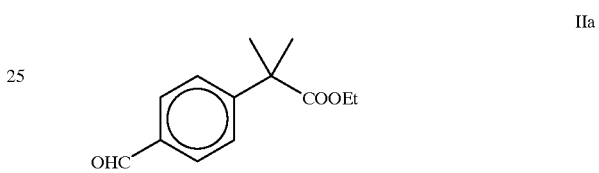

with from 1 to 1.5 equivalents of a Grignard reagent of formula IIIa

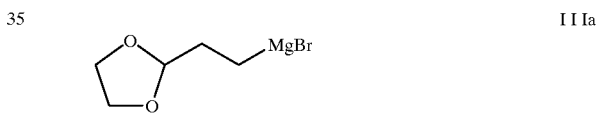

in an ethereal solvent to provide an intermediate of formula IVe

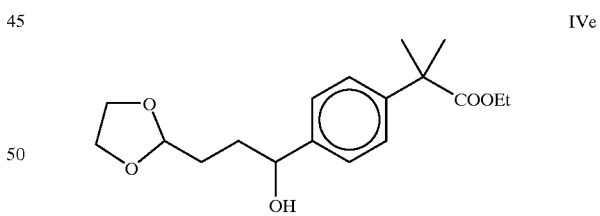

(The intermediate may be described by formula IV in which R¹ is a protected carboxyl and A is precursor of a formyl methyl group)

(b) deprotecting the intermediate by treating with aqueous acid (optionally a sulfonic acid ion exchange resin in the presence of water) to provide a mixture of aldehyde IVf and corresponding tautomeric lactol IVb:

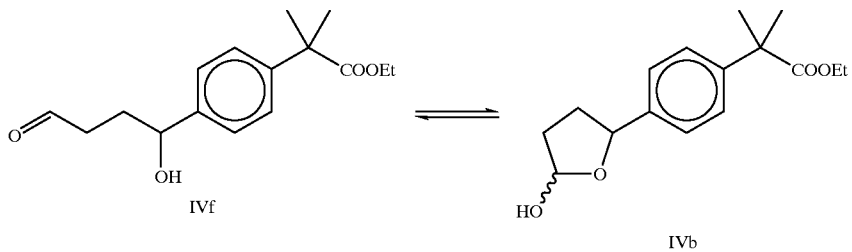

IVf ⇌ IVb (c) reductively aminating the aldehyde/lactol tautomeric mixture by treating with about one equivalent of α,α-diphenyl-4-piperidinemethanol and an excess of a borohydride reducing agent in a solvent to provide a compound of formula I in which $R^1$ is COOEt and $R^2$ is hydrogen;

(d) deprotecting by reacting with an excess of aqueous base, preferably an alkali metal hydroxide; and (e) recovering terfenadine carboxylate by acidifying and filtering.

In another aspect, the invention relates to compounds of Formula IVd

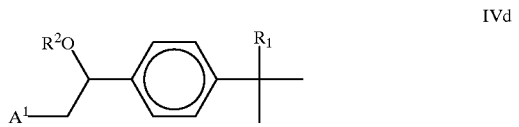

IVd in which: (1) $R^1$ is chosen from the group consisting of

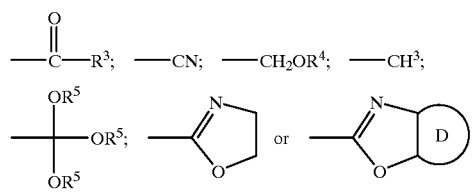

wherein D represents the residue of a 5- or 6-membered, saturated or aromatic ring; (2) $R^2$ is chosen from hydrogen, trialkylsilyl, benzyl, tetrahydropyran-2-yl, lower-alkylcarbonyl, arylcarbonyl and arylmethyl, wherein the aryl group is phenyl optionally substituted with from one to three substituents each independently selected from the group consisting of lower alkyl, lower alkoxy, and halo; (3) $R^3$ is chosen from alkoxy, wherein the alkoxy group contains from one to about 8 carbon atoms; alkenyloxy, wherein the alkenyloxy group contains from one to about 4 carbon atoms; arylmethoxy, wherein the aryl group is phenyl optionally substituted with from one to three substituents each independently selected from the group consisting of lower alkyl, lower alkoxy, and halo; (4) —$NR^6R^7$, wherein $R^4$, $R^5$, $R^6$ and $R^7$ are as defined above, and (5) $A^1$ is chosen from the group consisting of formylmethyl, vinyl, ethynyl, vinylmethyl, cyanomethyl, 2,2-di(lower-alkoxy)ethyl; (1,3-dioxolan-2-yl)methyl; (1,3-dioxan-2-yl)methyl; (1,3-dioxetan-2-yl)methyl; and (1,3-benzodioxolan-2-yl)methyl.

In another aspect, the invention relates to compounds of Formula VI and IVg and IX

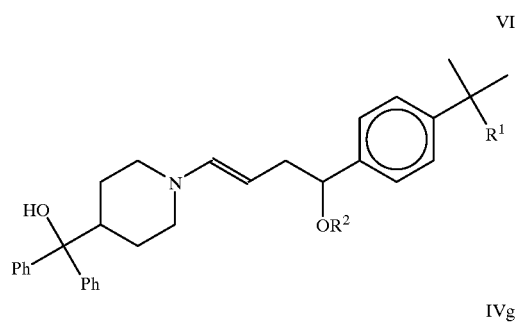

VI

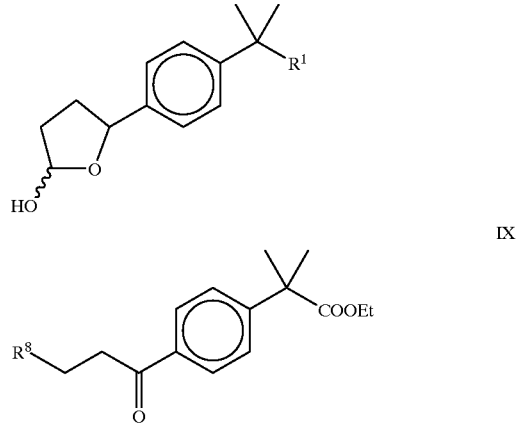

IVg

IX wherein $R^1$ to $R^7$ are as defined above for IVd and $R^8$ is OHC— or

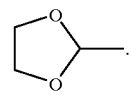

The compounds are useful as intermediates in the synthesis of antihistamines.

DETAILED DESCRIPTION OF THE INVENTION

The term "lower" when used herein in connection with "alkyl" or "alkoxy" designates a straight or branched chain containing one to about four carbon atoms. The configuration of any carbon—carbon double bond appearing herein is selected for convenience only and is not intended to designate a particular configuration; thus a carbon—carbon double bond depicted arbitrarily herein as trans may be cis, trans, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

In the case of the present invention, the functionalities that must be protected are carboxylic acids and alcohols. Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10–86) and "Protection for the Carboxyl Group" (pages 152-end).

A generalized synthetic scheme showing the various interrelated processes of the invention is presented in Scheme A:

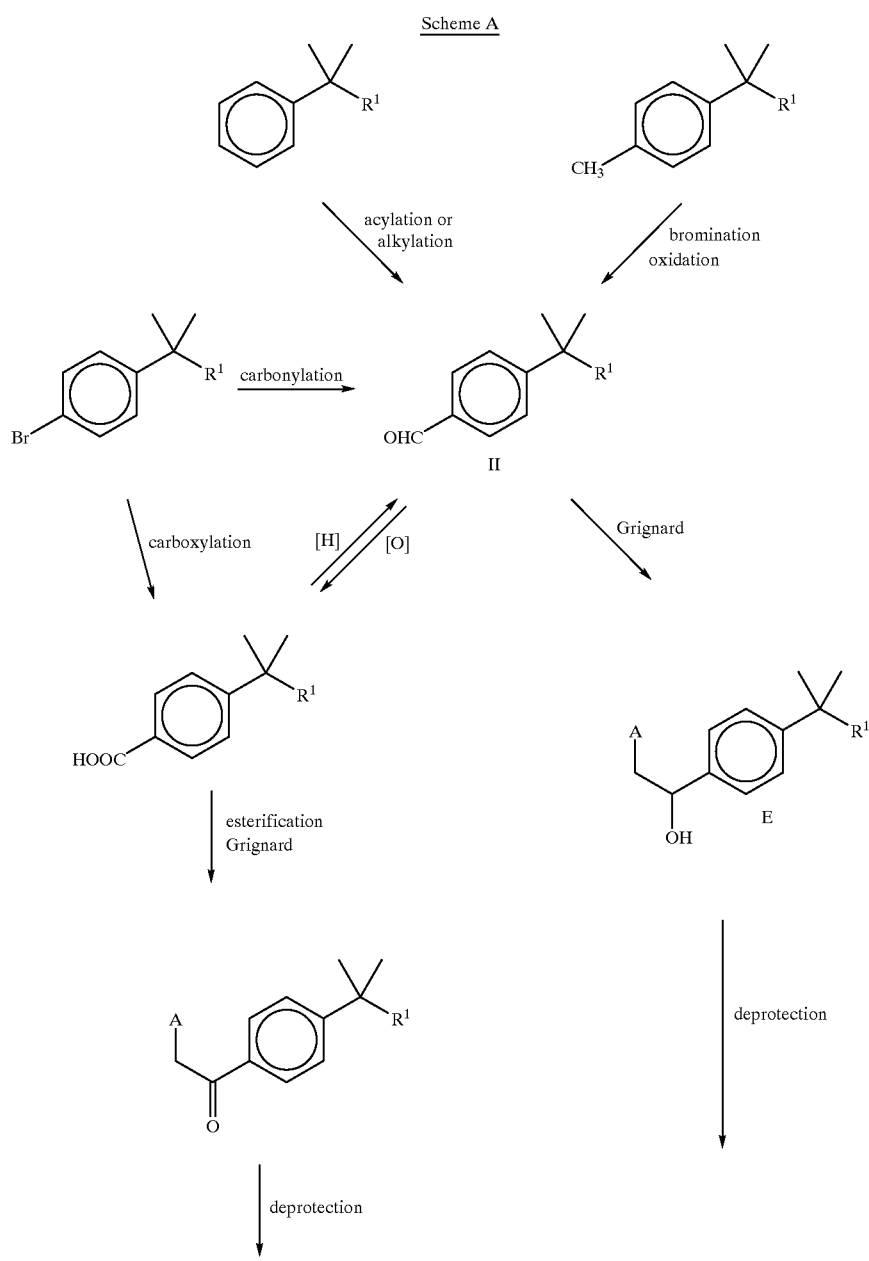

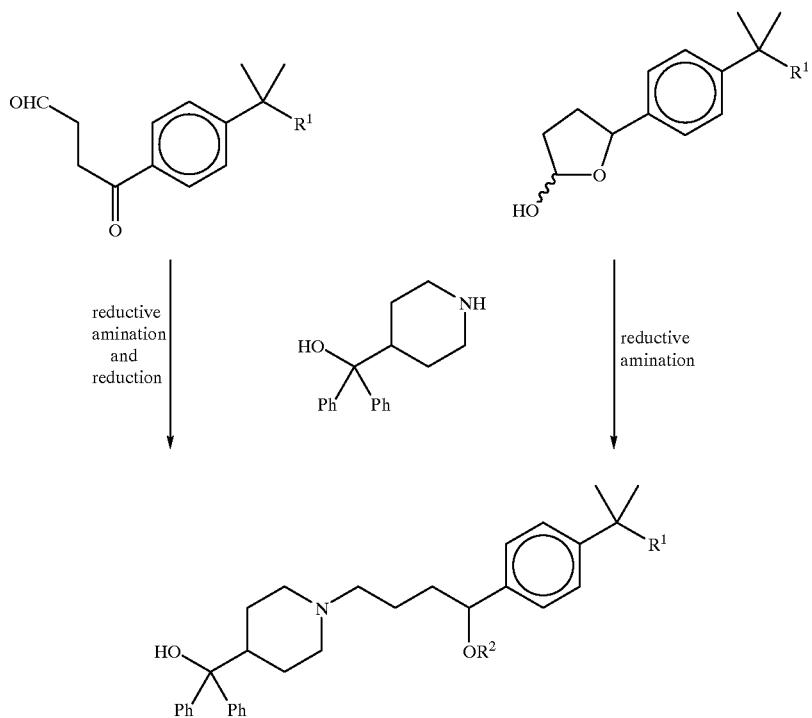

The process of the invention can be carried out using a compound of the general Formula II wherein $R^1$ is substantially inert to the conditions used in the step that involves nucleophilic addition of a compound of Formula III to the formyl group of the compound of Formula II. Suitable $R^1$ groups include those that provide esters (e.g., ethenyloxycarbonyl, alkoxycarbonyl wherein the alkoxy group contains from one to about 8 carbon atoms, and arylmethoxycarbonyl wherein the aryl group is phenyl optionally substituted with from one to three substituents each independently selected from the group consisting of lower alkyl, lower alkoxy, and halo), amides (e.g., aminocarbonyl, mono- or dialkylaminocarbonyl wherein each alkyl group is independently lower alkyl, benzylaminocarbonyl, and the like), oxazolines (e.g., 2-(1-oxa-3-azacyclopent-2-enyl, optionally annelated with propenyl, butenyl, or benzo), nitriles (cyano), and orthoesters (e.g., trialkoxymethyl wherein each alkoxy group independently contains from 1 to about 8 carbon atoms); protected hydroxymethyl (e.g., trialkylsilyloxymethyl wherein each alkyl group independently contains one to about 6 carbon atoms, —$CH_2OLi$, benzyloxymethyl, tetrahydropyranyl-2-oxymethyl, and the like), and methyl.

Compounds of Formula II can be prepared in several steps from commercially available starting materials (e.g., p-tolylacetic acid or its esters, alkyl phenylacetates, p-bromophenylacetic acid and its esters, and the like) using methods well known to those skilled in the art. The compound of Formula II in which $R^1$ is an ethyl ester is known in the art [See Maillard et al. Chim. Ther. 8, 487–494 (1973).] It may be prepared as described below from ethyl 2-p-tolyl-2-methylpropionate by bromination and treatment with hexamethylenetetramine or from ethyl 2-phenyl-2-methylpropionate by treatment with dichloromethylmethylether and $TiCl_4$. The starting material for the $TiCl_4$ alkylation is cheaper than for the bromination/oxidation, but the alkylation is not regiospecific; however the para-aldehyde can be obtained readily in one crystallization of the bisulfite addition product.

Compounds of Formula II may also be prepared from the appropriately functionalized iodo- or bromoaryl compound by carbonylation in the presence of tin hydride and palladium according to the procedure of Baillargeon and Stille [J. Am. Chem. Soc. 105, 7175–7176 (1983) and J. Am. Chem. Soc. 108, 452–461 (1986)], which are incorporated herein by reference.

The addition of three carbons to the aldehyde involves a compound of Formula III, (MX) [$CH_2$—A]$_n$. The moiety A in a compound of Formula III can be any moiety that can be converted to a formylmethyl group. Suitable groups A include: vinyl, which can be converted to formylmethyl by hydroboration/oxidation; vinylmethyl or (substituted-vinyl)methyl, which can be converted to formylmethyl by oxidation with ozone, ruthenium tetroxide/sodium periodate, permanganate, and the like; cyanomethyl, which can be converted to formylmethyl by reduction with diisobutylaluminum hydride; and acetal-containing moieties such as 2,2-(dialkoxy)ethyl. Particularly suitable alkoxy groups include dimethoxyl, diethoxyl and cyclic acetals such as (1,3-dioxacyclopent-2-yl)methyl, (1,3-dioxacyclohex-2-yl)methyl; (1,3-dioxacyclobut-2-yl)methyl, and (1,3-dioxa(benzo)cyclopent-2-yl)methyl, all of which can be converted to formylmethyl by way of acid-catalyzed hydrolysis of the acetal group. As shown below, the acetal may be hydrolyzed with mineral acid or with a sulfonic acid ion exchange resin, such as Amberlyst® or Dowex 50®, in the acid form.

Suitable groups for use as the moiety MX in a compound of Formula III include $Li^+$, $MgX^+$ or $ZnX^+$ wherein X is iodo, bromo, or chloro, $CeCl_2^+$ and $CuLi^{++}$. The MX group and the protected formylmethyl group of a compound of Formula III are readily selected by those skilled in the art to be compatible. For example, groups that render the compound strongly nucleophilic, such as MgBr, are not preferred when A is an electrophile such as cyanomethyl; however, MX may be, e.g., CuLi++ when A is cyanomethyl. Compounds of Formula III can be prepared using methods well known to those skilled in the art, e.g., from the corresponding compound having bromo in place of MX.

In the step in which a compound of Formula II is contacted with a compound of Formula III, the compound of Formula III is preferably prepared in a suitable inert solvent (e.g., an ethereal solvent such as tetrahydrofuran, diethyl ether, diisopropyl ether, diisobutyl ether, or dimethoxyethane) and added with stirring to a solution of a compound of Formula II in an inert solvent. Preferably the temperature of the reaction is controlled in order to avoid undesired side reactions, and the rate of addition is controlled in order to maintain the controlled temperature throughout the addition.

This step may optionally involve an additional step of protecting the hydroxy group that results from the nucleophilic addition to the aldehyde. Suitable protected hydroxy groups can be readily selected and incorporated by those skilled in the art, and include esters (e.g., —OR² wherein R₂is lower alkylcarbonyl, benzoyl, substituted benzoyl wherein the substituent is lower alkyl, lower alkoxy, or halo) or ethers (e.g., —OR² wherein R² is benzyl or substituted benzyl wherein the substituent is lower alkyl, lower alkoxy, or halo).

Two alternative pathways are shown in parallel from II to product in Scheme A: the right branch, described above, proceeds through intermediates in which the oxygen adjacent the benzene ring is in the alcohol oxidation state; the left branch proceeds through intermediates in which the oxygen adjacent the benzene ring is in the ketone oxidation state.

According to this second alternative, one may prepare the keto-aldehyde VIII corresponding to the hydroxy-aldehyde IVf.

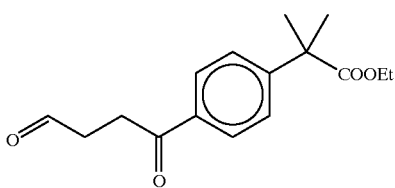

VIII

The aldehyde may then be selectively, reductively aminated with α,α-diphenyl-4-piperidinemethanol and the ketone may be reduced subsequently or concomitantly.

Although the keto-aldehyde VIII may be prepared by oxidation of the alcohol IVe and subsequent deprotection of the acetal or protected formyl group, it may also be prepared directly from the carboxylic acid corresponding to IIa, as shown in Scheme A, by Grignard addition to an acid derivative, such as an ester, followed by deprotection of the formyl equivalent. We have observed that the aldehyde IIa oxidizes to the carboxylic acid in air, making carboxylic acid derivatives readily accessible. Alternatively, the carboxylic acid or, an ester thereof, may be synthesized from the corresponding iodo- or bromoaryl compound by carbonylation in the presence of a palladium catalyst; an example of this procedure is given by Baldwin et al. [*Tetrahedron* 42, 3943–3956 (1986) at page 3951]. The carboxylic acid can be derivatized by the procedure of Weinreb [*Tetrahedron Letters* 22, 3815–3818 (1981)] with methoxymethylhydroxylamine or by the procedure of Rappoport [*J. Org. Chem.* 61, 6071–6074 (1996)] with methanesulfonic acid and dihydrofuran. The foregoing references are incorporated herein by reference. In either case, the resulting ester can be reacted with the Grignard IIIa to provide the aldehyde-protected keto-aldehyde.

In the next step in the sequence, the protected formylmethyl group is deprotected to afford a compound of general Formula IVa, which, when R² is hydrogen, exists predominantly as the lactol tautomer IVb rather than the hydroxyaldehyde IVf. In the "left branch' synthesis via the ketone, the deprotected keto-aldehyde obviously does not cyclize. Suitable methods of deprotection include those discussed above in connection with compounds of Formula III. The hydroxyaldehyde and the lactol IVb are both suitable for use in reductive amination. Under most conditions the aldehyde/lactol equilibrium lies far to the right, and the lactol predominates by as much as 98:2. Similarly, the ketoaldehyde VIII may be reductively aminated (at the aldehyde) and reduced (at the ketone) simultaneously, or at least in the same pot.

The reductive amination process involves a first step of contacting the aldehyde or lactol with α,α-diphenyl-4-piperidinomethanol (Formula V above). The reaction is preferably carried out by adding an excess of the compound of Formula V to a solution of IVf/IVb in a hydroxylic solvent (e.g., methanol, ethanol, 2-propanol) to afford an addition product that comprises an enamine of formula VI or a mixture of the enamine VI, the iminium salt VIa and the α-hydroxyamine VIb

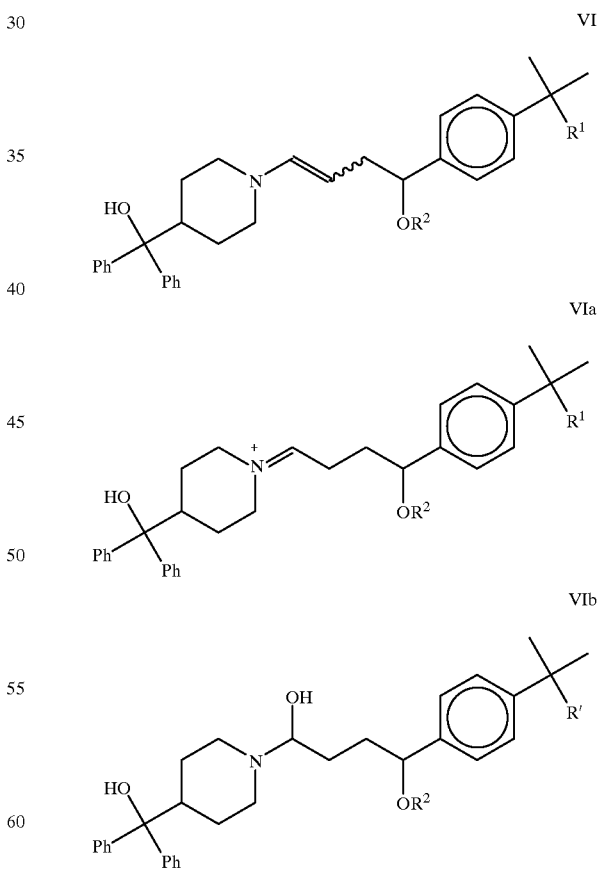

The enamine VI may be in the cis or trans configuration or may be a mixture of the two.

The addition product can be reduced to provide a compound of Formula I. The reduction can be carried out using conventional methodology (e.g., sodium borohydride, sodium cyanoborohydride, diisobutylaluminum hydride, lithium aluminum hydride, sodium acetoxyborohydride, or catalytic hydrogenation using platinum, palladium, or nickel as catalyst). It is preferred that the reduction be carried out without isolation of the intermediate addition product.

In another embodiment of this invention, a compound of Formula IVb is oxidized to provide the corresponding lactone of Formula IVc

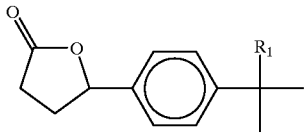

IVc

The oxidation can be carried out using conventional oxidizing agents such as pyridinium dichromate, pyridinium chlorochromate, or DMSO/triethylamine.

The lactone of Formula IVc can be converted to a compound of Formula VI by reduction with reducing agents known to convert esters to aldehydes (e.g., diisobutylaluminum hydride) followed by addition of α,α-diphenyl-4-piperidinomethanol and appropriate reduction of the product as described above.

In a preferred embodiment of the invention $R^1$ is a protected carboxy group. For example, $R^1$ can constitute functionality that provides esters (e.g., ethenyloxycarbonyl, allyloxycarbonyl, methoxycarbonyl, ethoxycarbonyl and benzyloxycarbonyl or substituted benzyloxycarbonyl), amides (e.g., aminocarbonyl, mono- or dialkylaminocarbonyl wherein each alkyl group is independently lower alkyl, benzylaminocarbonyl, and the like), oxazolines (e.g. 1-oxa-3-azacyclopent-2-enyl, optionally annelated with propenyl, butenyl, or benzo), nitriles (cyano), and orthoesters (e.g., trialkoxymethyl wherein each alkoxy group independently contains from 1 to about 8 carbon atoms). These protected carboxy groups can be readily deprotected to provide a carboxy group, thus affording the antihistamine terfenadine carboxylate (Formula B).

In yet another preferred embodiment of the invention $R^1$ of Formula I is a protected hydroxymethyl group. For example, $R^1$ can constitute trialkylsilyloxymethyl wherein each alkyl group independently contains one to about 6 carbon atoms, —$CH_2OLi$, benzyloxymethyl, tetrahydropyranyl-2-oxymethyl, and the like. These protected hydroxymethyl groups can be readily deprotected to provide a hydroxymethyl group, thus affording the antihistaminic compound of Formula D:

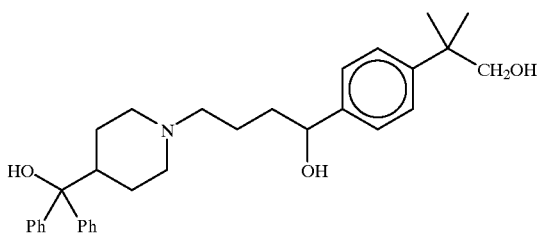

The invention is illustrated by the following Examples.

EXAMPLES

Ethyl 2-p-Tolyl-2-Methyl Propionate: Sodium hydride (17.6 g, 60% by wt, 0.43 mol) was washed with hexane (2×60 mL) to remove mineral oil and was suspended in anhydrous THF (200 mL) under nitrogen. A solution of ethyl p-tolyl acetate (17.8 g, 0.10 mol) in THF (40 mL) was slowly added to the above suspension in 20 min and the resulting suspension was stirred at 22° C. for 30 min. Iodomethane (52.4 g, 0.37 mol) was added dropwise to the above suspension over 30 min at 22° C. (the reaction is exothermic and the reaction flask should be equipped with a condenser and cooled with a water bath). After 3 h stirring, the reaction mixture was quenched with florisil (12 g), and stirred for 30 min. The reaction mixture was filtered through a celite pad. The reaction flask was rinsed with THF (50 mL) and used to wash the celite pad. The filtrate was concentrated to give a residue, which was partitioned between MTBE (200 mL) and water (150 mL). The organic layer was washed with brine (40 mL), dried over $Na_2SO_4$ (20 g) and concentrated to give an oil. The crude product was used for the next step without purification. $^1H$ NMR ($CDCl_3$) d 1.10–1.150 (t, J=7.5 Hz, 3H), 1.62 (s, 6H), 2.38 (s, 3H), 4.11–4.20 (q, J=7.5 Hz, 2H), 7.12–7.30 (m, 4H).

The reaction was repeated on a larger scale as follows:

Sodium hydride (43 g, 95% by wt, 1.68 mol) was washed and suspended in anhydrous THF (1200 mL) under nitrogen while cooled with ice-water bath. A solution of ethyl p-tolyl acetate (120 g, 0.67 mol) in THF (40 mL) was added to the above suspension slowly over 20 min, and the resulting suspension was stirred at 22° for 30 min. Iodomethane (23 g, 1.68 mol) was added dropwise to the above suspension over 1.5 h at 22° C. (the reaction is exothermic and the reaction flask should be equipped with a condenser and cooled with a water bath). After the addition, the reaction mixture was heated at reflux for 2 h, and was quenched with water (1.5 L), very slowly to destroy the excess NaH at the beginning, while cooling with an ice-water bath, then extracted with hexane (4×400 mL). The extracts were combined and washed with water, and brine, then dried over $Na_2SO_4$ (20 g) and concentrated to give an oil (134 g, 98% yield). The crude product was used in the next step without purification.

Ethyl 2-(4-Bromomethylphenyl)-2-Methyl Propionate: To a solution of ethyl 2-p-tolyl-2-methyl propionate (22 g, 106 mmol) in carbon tetrachloride (200 mL) NBS (22.8 g, 128 mmol) and benzoyl peroxide (0.5 g) was added at 22° C. The reaction mixture was heated under reflux for 14 h. The reaction mixture was cooled to 22° C. and filtered, the filtrate was concentrated to give an oily residue, which was passed through a short column of silica gel to remove the additional succinimide using EtOAc/hexane (1:9) to give an oil (31 g). The material was used for next the reaction without further purification. $^1H$ NMR ($CDCl_3$) d 1.19–1.40 (t, J=7.2 Hz, 3H), 1.59 (s, 6H), 4.08–4.18 (q, J=7.2, 2H) 4.50 (s, 2H), 7.30 –7.38 (m, 4H).

Ethyl 2-(4-Formylphenyl)-2-Methylpropionate (formula II; $R^1$=COOEt): Hexamethylenetetramine (3.5 g) was dissolved in chloroform (50 mL) and followed by addition of ethyl 2-(4-bromethylphenyl)-2-methyl propionate (5.7 g) in chloroform (30 mL). The reaction mixture was stirred at 22° C. for 30 min and heated at reflux for 14 h, and concentrated to give a solid residue, without purification, the solid residue was suspended in water (100 mL) and heated at reflux for 15 h. The reaction mixture was then cooled to rt, extracted with EtOAc (30 mL), the organic phase was concentrated to give a crude oil, which was purified by flash chromatography (EtOAc/hexane 1:9) to give 1.57 g (55) analytically pure product. $^1H$ NMR ($CDCl_3$) d 1.12–1.17 (t, J=7.2 Hz, 3H), 1.57 (s, 6H), 4.06–4.13 (q, J=7.2 Hz, 2H), 7.46–7.49 (d, J=8.7 Hz, 2H), 7.80–7.83 (d, J=8.7 Hz, 2H), 9.96 (s, 1H).

Ethyl 2-(4-Formylphenyl)-2-Methylpropionate (formula II; R[1]=COOEt) (alternate synthesis): Ethyl 2-phenyl-2-methylpropionate (10 g) was dissolved in 50 mL of dichloromethane and cooled to 5° C. Titanium tetrachloride (10.5 mL) and 1,1-dichloromethyl methyl ether (7.5 mL) were added and the mixture was stirred at room temperature for 60 hours. The resulting dark solution was diluted with 50 mL of dichloromethane and washed twice with 50 mL of water. The organic solution was concentrated to give an oil which was treated with 30 mL of saturated aqueous sodium bisulfite solution for 12 hours. The precipitate was collected by filtration, washed with hexane, suspended in ethyl acetate and treated with excess potassium carbonate. The organic phase was separated, dried with sodium sulfate and stripped to provide 2 g of product.

Ethyl 2-[3-(1,3-Dioxolan-2-yl)-1-Hydroxy-Propylphenyl]-2-Methylpropionate: The Grignard reagent was prepared by addition of 2-(2-bromoethyl)-1,3-dioxolane (4.32 g, 24 mmol) in THF (60 mL) to magnesium powder (0.62 g) over 10 min while keeping the reaction temperature below 50° C. by cooling with a water bath (10–20° C.). The reaction mixture was stirred for an additional 1 h. The Grignard reagent was then added to a solution of ethyl 2-(4-formylphenyl)-2-methylpropionate (4.4 g, 20 mmol) in THF (20 mL) at −78° C. via syringe over 5 min. The reaction mixture was then warmed to 22° C. over 25 min and stirred for 10 min at that temperature. The reaction mixture was poured into water (60 mL), followed by extraction with EtOAc (2×100 mL). The extracts were combined and washed with water (30 mL), dried over $Na_2SO_4$, and evaporated. The crude product can be used for the next step without purification. It was purified by chromatography (EtOAc/Hexane 4:6) to give ethyl 2-[3-(1,3-dioxolan-2-yl)-1-hydroxy-propylphenyl]-2-methylpropionate (4.8 g, 75% yield). $^1$H NMR (CDCl$_3$) d 1.15–1.19 (t, J=7.1 Hz, 3H), 1.55 (s, 6H), 1.65–1.90 (m, 4H), 2.92 (broad s, 1H), 3.75–388 (m, 2H), 3.90–3.97 (m, 2H), 4.06–4.13 (q, J=7.0 Hz, 2H), 4.65–4.69 (m, 1H), 4.86–4.89 (m, 1H). 7.29 (s, 4H).

The reaction was repeated on a larger scale as follows:

The Grignard reagent was prepared by the addition of 2-(2-bromoethyl)-1,3-dioxolane (68 g, 377 mmol) in THF (100 mL) to magnesium powder (9.5 g, 395 mmol) in THF (600 mL) over 45 min while keeping the reaction temperature below 50° C. by cooling with a water bath (10–20° C.). The reaction mixture was stirred for 1 h after the addition. The Grignard reagent was then cooled to 10 to 15° C. with an ice-water bath, followed by the addition of a solution of ethyl 2-(4-formlyphenyl)-2-methylpropionate (60 g, 272 mmol) in THF (20 mL) via syringe over 20 min. The reaction was exothermic, and the inner temperature increased to 25° C., even though the flask was cooled with an ice-water bath. After the addition, the reaction mixture was stirred for 10 min at 22° C. The reaction mixture was quenched with water (15 mL, caution!), then with saturated ammonium chloride solution (200 mL), and extracted with EtOAC (300 mL, 60 mL). The extracts were combined and washed with water (30 mL), dried over $Na_2SO_4$, and evaporated. The crude product (92 g 105% by weight) was used for the next step without purification.

Hydrolysis of Ethyl 2-[3-(1,3-Dioxolan-2-yl)-1-Hydroxy-Propylphenyl]-2-Methylpropionate: To a solution of ethyl 2-[3-(1,3-dioxolan-2-yl)-1-hydroxy-propylphenyl]-2-methylpropionate (0.34 g) in THF (5 mL) at 22° C., 5% HCl (5 mL) was added. The reaction mixture was heated at reflux for 1 h. The reaction mixture was cooled to 22° C. extracted with EtOAc(2×20 mL), and concentrated. The remaining oil residue was passed through a column of silica gel using EtOAc/hexane (3:7) to give a mixture (1:1) of cis and trans lactols (0.2 g, 68%) containing <5% aldehyde determined by $^1$H NMR.

Alternate Hydrolysis of Ethyl 2-[3-(1,3-Dioxolan-2-yl)-1-Hydroxy-Propylphenyl]-2-Methylpropionate: To a solution of ethyl 2-[3-(1,3-dioxolan-2-yl)-1-hydroxy-propylphenyl]-2-methylpropionate (90 g) in 900 mL of acetone at 22° C. was added 150 g of Amberlyst 15® in the H$^+$ form and 180 mL of water. The reaction mixture was degassed and heated to 50° C. for 13 hours under argon atmosphere. The reaction mixture was concentrated to remove the solvent and the residue extracted with EtOAc (80 mL), washed with water (2×150 mL) and concentrated to give 79 g of oil. Proton NMR analysis of the oil indicated 77% product, 14% starting material and 8% of a partially hydrolyzed by-product. The residue was redissolved in 600 mL of acetone to which 100 g of Amberlyst 15® and 150 mL of water were added. The mixture was heated at 40°–45° C. for 60 hours, and worked up as before to provide 77 g of product pure enough for use in the next step. If desired it may be passed through a column of silica gel using EtOAc/hexane (3:7) to give a mixture (1:1) of cis and trans lactols in 85% yield. The lactol contains less than 5% of the tautomeric aldehyde as determined by $^1$H NMR.

Ethyl 4-[1-Hydroxy-4-[4-(Hydroxydiphenylmethyl)-1-Piperidinyl]butyl]-α,α-Dimethylbenzeneacetate: To a solution of the mixture of cis/trans lactols from above (4.8 g) in methanol (100 mL), α,α-diphenyl-4-piperidinomethanol (4.1 g ) was added. The reaction mixture was heated to 75° C. for 1 h. The reaction solution was then cooled with an ice-water bath to 4° C., and sodium borohydride (0.75 g) was added over 5 min period. The reaction mixture was stirred at 22° C. for 30 min. The reaction was quenched by addition of water (10 mL) and concentrated to remove the solvent. The residue was dissolved in water (50 mL) and extracted with EtOAc (60 mL), the organic phase was concentrated, the crude product was passed through a short column of silica gel (EtOAc/hexane 3:7) to give desired product (4.5 g). $^1$H NMR (CDCl3) d 1.12–1.17 (t, J=7.1 Hz), 1.53 (s, 6H), 1.40–1.80 (m, 6H), 1.88–2.10 (m, 4H), 2.3–2.50 (m, 4H), 2.93–2.96 (d, J=10 Hz, 1H), 3.11–3.15 (d, J=11 Hz), 4.04–4.11 (q, J=7.3 Hz, 2H), 4.56–4.59 (dd, J1=2.7 Hz, J2=8.4 Hz, 1H), 7.15–7.18 (m, 2H), 7.25–7.30 (m, 8H), 7.45–7.50 (m, 4H).

The foregoing reaction was repeated on a larger scale as follows:

To a solution of the mixture cis/trans (77 g crude 0.200 mol) in methanol (650 mL) was added α,α-diphenyl-4-piperidinemethanol (55 g, 0.206 mol). The reaction mixture was heated at 50° C. for 1 h (A clear solution was obtained). The reaction solution was then cooled with an ice-water bath to 10 to 15° C., and sodium borohydride (15 g,) was added over 15 min. The reaction was exothermic and the inner temperature rose to 40° C. The reaction mixture was stirred for 30 min after the addition of NaBH$_4$. The reaction was quenched by addition of water (10 mL), and concentrated to remove the solvent to give a solid residue. It was suspended in water (500 mL) and extracted with ethyl acetate (400 mL, 200 mL). The combined organic phases were washed with water (100 mL), brine (50 mL), dried over $Na_2SO_4$ for 1 h, filtered, the filtrate was concentrated to give a thick oil which contained about 50 mL of EtOAc. To it was added hexane (400 mL) with stirring, and a white precipitate was collected by filtration. The solid was washed with hexane (60 mL and dried to give 105 g crude product (91 pure by HPLC, 66.4% overall yield from the aldehyde). The crude product was used for next step, or could be purified by passing through a short column of silica gel (EtOAc) to give the desired product (85%).

4-[1-Hydroxy-4-[4-(Hydroxydiphenylmethyl)-1-Piperidinyl]butyl]-α,α-Dimethylbenzeneacetic Acid: Ethyl 4-[1-hydroxy-4-[4-(hydroxydiphenylmethyl)-1-piperidinyl]butyl]-α,α-dimethylbenzeneacetate (0.5 g) was dissolved in MeOH (10 mL), and sodium hydroxide solution (0.35 g, water 3 mL) was added. The reaction mixture was heated at reflux for 5 h, and cooled to 22° C., followed by the addition of acetic acid to reach a pH 4–5. MeOH (5 mL) was added to the solution and stirred for 1 h. The precipitate was collected by filtration to give 0.42 g of 4-[4-[4-(hydroxydiphenylmethyl)-1-piperidinyl]-1-hydroxybutyl]-α,α-dimethylbenzeneacetic acid. $^1$H NMR (DMSO-d6) d 1.45–1.49(m, 2H), 1.67 (s, 6H), 1.67–1.78 (m, 6H), 2.12–2.20 (m, 2H), 2.45–2.50 (m, 2H), 2.68–2.78 (m 3H), 3.10 (broad s, 2H), 4.71 (m, 1H), 5.50 (broad s, 1H), 7.35–7.40 (m, 2H), 7.45–7.55 (m, 8H), 7.76–7.78 (m, 4H). MH$^+$ 502.3.

The foregoing reaction was repeated on a larger scale as follows:

Ethyl 4-[1-hydroxy-4-[4-(hydroxydiphenylmethyl)-1-piperidinyl]butyl]-α,α-dimethylbenzeneacetate (crude, 104 g, 196 mmol) was dissolved in MeOH (1 L), and sodium hydroxide solution (40 g, water 400 mL) was added. The reaction mixture was heated at reflux for 3 h, and cooled to 22° C., followed by addition of acetic acid (65 mL) to reach pH 4–5. A white precipitate appeared. The suspension was cooled to 0 to 5° C. and filtered and washed with water (60 mL) to yield a wet cake (160 g, 97.43% area by HPLC). The wet cake was transferred to a 2L flask, methanol was added (1.5 L), heated to reflux for 20 min, cooled to rt overnight, and filtered to collected the solid as wet cake (133 g). It was dried to give the product (80 g, 89% yield, cp 99.51%)

Fexofenadine HCl salt: To a suspension of ethyl 4-[1-hydroxy-4-[4-(hydroxydiphenylmethyl)-1-piperidinyl]butyl]-α,α-dimethylbenzeneacetate (80 g, 0.160 mol) in MeOH (200 mL) was added to a solution of HCl (1.57 M, 120 mL) at 0 to 5° C. (the salt formation was not exothermic, a clear solution was obtained). The reaction mixture was concentrated to remove most of the solvent (ca 250 mL) to give a thick oil. To it was added water (300 mL) to give a suspension, which was stirred to 15 min, heated to 55 to 60° C. for 15 min (the suspension remained), and cooled to rt overnight, then 0 to 5° C. for 2 h, filtered, and the wet cake washed with ethyl acetate (40 mL). The hydrochloride salt (78 g 90%) was obtained after drying the wet cake for 50 h at 45 to 50° C. under vacuum (1 mm Hg), cp. 99.4%, LOD 0.79 (50 to 150° C.).

Ethyl 2-[4-[3-(1,3-Dioxolan-2-yl)]-1-Oxopropyl]phenyl-2-Methylpropionate

To 4 g of ethyl 2-[4-[3-(1,3-dioxolan-2-yl)]-1-hydroxypropylphenyl]-2-methylpropionate (4 g, 12.5 mmol) in dichloromethane (50 mL) was added PDC (6.9 g) at rt. The reaction mixture was stirred for 15 h, and filtered through celite, the filtrate was concentrated to give a residue, which was passed through a short column of silica gel using EtOAc/hexane (4:6) as eluate to give 3.4 g (10.5 mmol) title product (84%). $^1$H NMR (CDCl$_3$) δ 1.16–1.20 (t, J=7.1 Hz, 3H), 1.59 (s, 6H), 2.10–2.17 (m, 2H), 3.08–3.13 (t, J=6.3 Hz, 1H), 3.86–3.98 (m, 4H), 4.09–416 (q, J=7.1 Hz, 2H), 5.03 (t, J=4.5 Hz, 1H), 7.41–7.44 (d, J=8.7 Hz), 7.94–7.97 (d, J=8.7 Hz, 2H). $^{13}$C δ 13.93, 26.27, 27.88, 32.38, 46.68, 60.92, 64.90, 103.35, 125.85, 128.10, 135.20, 149.94, 175.95, 198.74.

Ethyl 2-[4-(3-Formyl-1-Oxopropyl)]phenyl-2-Methylpropionate

Ethyl 2-[3-(1,3-dioxolan-2-yl)-1-oxopropylphenyl]-2-methylpropinate (0.31 g, 1 mmol) was dissolved in acetone (8 mL), followed by addition of 5% HCl (8 mL). The reaction mixture was stirred at rt for 5 h, and concentrated to remove acetone, the residue was extracted with ethyl acetate (10 mL), washed with water, brine, and concentrated to give the title compound (0.27 g, 1 mmol). $^1$H NMR (CDCl$_3$) δ 1.16–1.21 (t, J=7.1 Hz, 3H), 1.59 (s, 6H), 2.91–2.95 (t, J=6.3 Hz, 2H), 3.29–3.33 (t, J=6.3 Hz, 2H), 409–4.17 (q, J=7.1 Hz, 2H), 7.43–7.46 (d, J=8.7 Hz), 7.94–7.97 (d, J=8.7 Hz, 2H). $^{13}$C δ 13.86, 26.19, 30.82, 37.42, 46.64, 60.88, 125.89, 128.06, 134.66, 150.26, 175.82, 197.17, 200.49

Ethyl 2-(4-carboxylphenyl)-2-Methylpropinate

A solution of ethyl 2-(4-formylphenyl)-2-methylpropionate (1 g) in EtOAc (5 mL) was stirred in air for 24 h. The solvent was then removed to give a crude colorless solid as title compound (1 g). $^1$H NMR (CDCl$_3$) δ 1.16–1.21 (t, J=7.1 Hz, 3H), 1.61 (s, 6H), 4.10–4.17 (q, J=7.1 Hz, 2H), 7.44–7.47 (d, J=8.7 Hz), 8.07–8.09 (d, J=8.7 Hz, 2H), 12.0 (broad s, 1H). $^{13}$C δ 13.89,. 26.25, 46.77, 61.02, 125.82, 130.21, 150.80, 171.80, 176.03, 191.95.

Alternate Synthesis of Ethyl 4-[1-Hydroxy-4-[4-(Hydroxydiphenylmethyl)-1-Piperidinyl]butyl]α,α-Dimethylbenzeneacetate from ethyl 2-[4-(3-formyl-1-oxopropyl)]phenyl-2-methylpropinate Employing the same procedure as described about but replacing lactol (IVb) with ethyl 2-[4-[3-formyl-1-oxopropyl]phenyl]-2-methylpropionate as the starting material for the reductive amination, the title compound may be prepared.

What is claimed is:

1. A compound of Formula VI

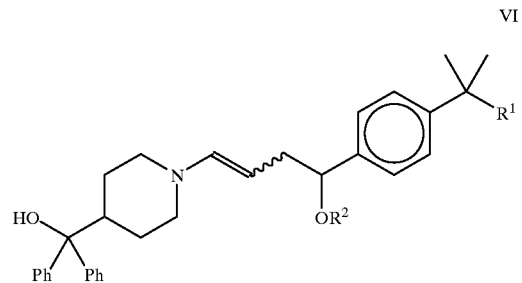

wherein

R$^1$ is chosen from the group consisting of

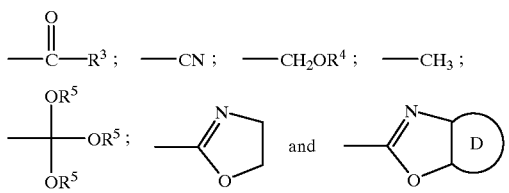

wherein D represents the residue of a 5- or 6-membered, saturated or aromatic ring;

R$^2$ is chosen from hydrogen, trialkylsilyl, benzyl, tetrahydropyran-2-yl, lower-alkylcarbonyl, arylcarbonyl and arylmethyl, wherein the aryl group is phenyl optionally substituted with from one to three substituents each independently selected from the group consisting of lower alkyl, lower alkoxy, and halo;

R³ is chosen from alkoxy, wherein the alkoxy group contains from one to about 8 carbon atoms; alkenyloxy, wherein the alkenyloxy group contains from one to about 4 carbon atoms; arylmethoxy, wherein the aryl group is phenyl optionally substituted with from one to three substituents each independently selected from the group consisting of lower alkyl, lower alkoxy, and halo; and —NR⁶R⁷;

R⁴ is chosen from trialkylsilyl, Li⁺, benzyl, tetrahydropyran-2-yl, lower-alkylcarbonyl, arylcarbonyl and arylmethyl, wherein the aryl group is phenyl optionally substituted with from one to three substituents each independently selected from the group consisting of lower alkyl, lower alkoxy, and halo;

R⁵ is alkyl of 1 to 6 carbons; and

R⁶ and R⁷ are chosen independently from hydrogen, alkyl of 1 to 8 carbons and benzyl.

2. A process of using a compound of formula VI

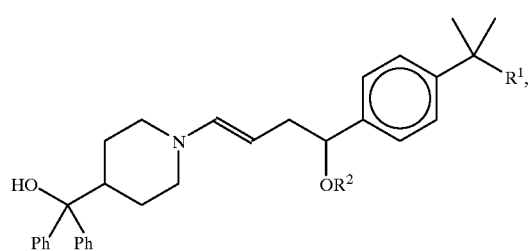

VI comprising reducing said compound of formula VI with a hydride or by catalytic hydrogenation to provide a compound of formula I

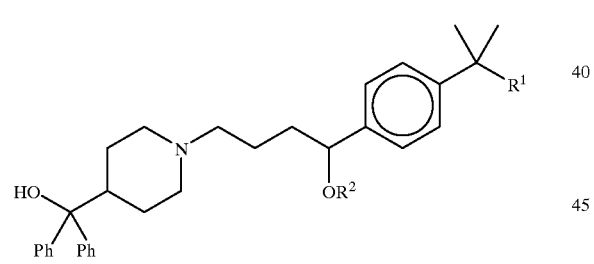

I wherein R¹ is chosen from the group consisting of

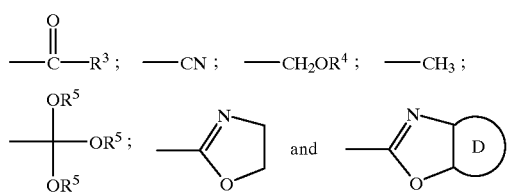

wherein D represents the residue of a 5- or 6-membered, saturated or aromatic ring;

R² is chosen from hydrogen, trialkylsilyl, benzyl, tetrahydropyran-2-yl, lower-alkylcarbonyl, arylcarbonyl and arylmethyl, wherein the aryl group is phenyl optionally substituted with from one to three substituents each independently selected from the group consisting of lower alkyl, lower alkoxy, and halo;

R³ is chosen from alkoxy, wherein the alkoxy group contains from one to about 8 carbon atoms; alkenyloxy, wherein the alkenyloxy group contains from one to about 4 carbon atoms; arylmethoxy, wherein the aryl group is phenyl optionally substituted with from one to three substituents each independently selected from the group consisting of lower alkyl, lower alkoxy, and halo; and —NR⁶R⁷;

R⁴ is chosen from trialkylsilyl, Li⁺, benzyl, tetrahydropyran-2-yl, lower-alkylcarbonyl, arylcarbonyl and arymethyl, wherein the aryl group is phenyl optionally substituted with from one to three substituents each independently selected from the group consisting of lower alkyl, lower alkoxy, and halo;

R⁵ is alkyl of 1 to 6 carbons;

R⁶ and R⁷ are chosen independently from hydrogen, alkyl of 1 to 8 carbons and benzyl.

3. A process according to claim 2 in which said reducing agent is a borohydride.

4. A process according to claim 2, wherein R¹ is protected hydroxymethyl or protected carboxyl and R² is hydrogen, further comprising the step of deprotecting R¹ to provide a compound of Formula B or D

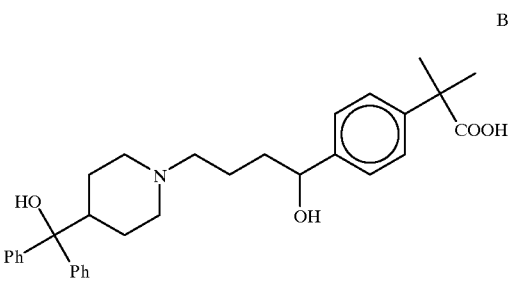

B

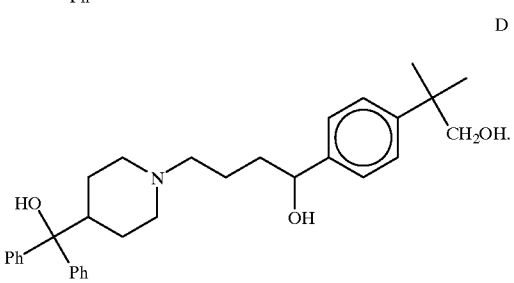

D

5. A process according to claim 2, wherein R¹ is protected hydroxymethyl or protected carboxyl and R² is a protecting group for hydroxyl, further comprising the steps of deprotecting R¹ and R² to provide a compound of Formula B or D

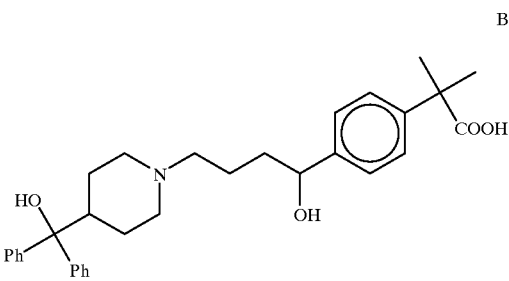

B

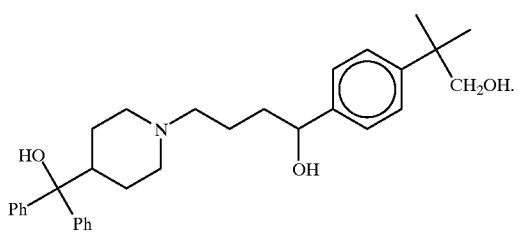

6. A process according to claim 2, wherein $R^1$ is methyl and $R^2$ is a protecting group for hydroxyl, further comprising the step of deprotecting $R^2$ to provide a compound of Formula T

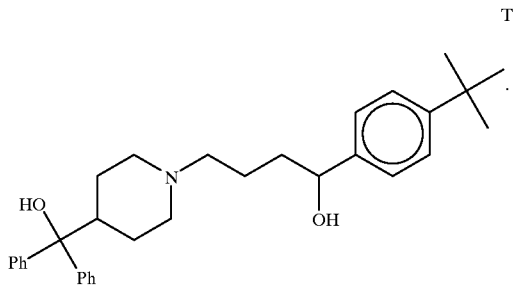

7. A process according to claim 2 wherein $R^2$ and $R^4$ are the same, and deprotection of —$OR^2$ and —$CH_2OR^4$ is carried out in a single step.

8. A process according to claim 2 comprising the sequential steps of:
(a) reacting a compound of formula

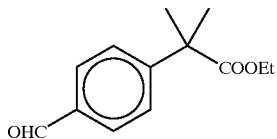

with from 1 to 1.5 equivalents of a Grignard reagent of formula

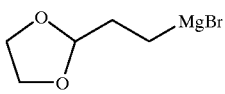

in an ethereal solvent to provide an intermediate of formula

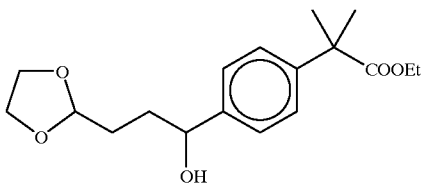

(b) deprotecting said intermediate by treating with aqueous acid to provide the lactol of formula:

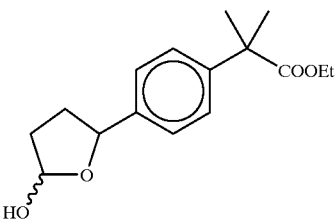

(c) reductively aminating said lactol by treating with about one equivalent of α,α-diphenyl-4-piperidinemethanol and an excess of a borohydride reducing agent in a solvent to provide a compound of formula I in which $R^1$ is COOEt and $R^2$ is hydrogen;

(d) deprotecting said compound of formula I in which $R^1$ is COOEt and $R^2$ is hydrogen by reacting with an excess of aqueous base; and (e) recovering terfenadine carboxylate by acidifying.

* * * * *

UNITED STATES PATENT AND TRADEMARK OFFICE
CERTIFICATE OF CORRECTION

PATENT NO. : 6,147,217
DATED : November 14, 2000
INVENTOR(S) : Senanayake et al.

It is certified that error appears in the above-identified patent and that said Letters Patent are hereby corrected as shown below:

Column 6, line 14, after the word When, delete (R1) and insert - - R2- -, and after the dash , delete (OR1) and insert - - OR2 - -

Signed and Sealed this

Eighth Day of May, 2001

Attest:

NICHOLAS P. GODICI

Attesting Officer Acting Director of the United States Patent and Trademark Office